(12) United States Patent
Weiss et al.

(10) Patent No.: US 10,413,441 B2
(45) Date of Patent: Sep. 17, 2019

(54) COLOSTOMY BALLOON PLUG

(71) Applicant: INCONTINENT CONTROL DEVICES, INC., Houston, TX (US)

(72) Inventors: Stephen Joel Weiss, Houston, TX (US); David Simovich, Aventura, FL (US)

(73) Assignee: Incontinent Control Devices, Inc., Houston, TX (US)

( * ) Notice: Subject to any disclaimer, the term of this patent is extended or adjusted under 35 U.S.C. 154(b) by 770 days.

(21) Appl. No.: 14/944,408

(22) Filed: Nov. 18, 2015

(65) Prior Publication Data
US 2017/0135846 A1   May 18, 2017

(51) Int. Cl.
*A61F 5/445* (2006.01)
*A61F 5/441* (2006.01)

(52) U.S. Cl.
CPC .............. *A61F 5/445* (2013.01); *A61F 5/441* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,937,224 A | * | 2/1976 | Uecker | A61F 5/445 604/101.05 |
| 4,351,322 A | * | 9/1982 | Prager | A61F 5/4404 600/32 |
| 4,381,765 A | * | 5/1983 | Burton | A61F 5/445 600/32 |
| 4,662,890 A | * | 5/1987 | Burton | A61F 5/445 128/899 |
| 4,721,508 A | * | 1/1988 | Burton | A61F 5/445 604/103.03 |

(Continued)

FOREIGN PATENT DOCUMENTS

| | | | | | |
|---|---|---|---|---|---|
| CN | 202682106 | * | 1/2013 | ............... | A61F 5/00 |
| CN | 202682106 U | * | 1/2013 | ............... | A61F 5/00 |

(Continued)

*Primary Examiner* — Tatyana Zalukaeva
*Assistant Examiner* — Guy K Townsend
(74) *Attorney, Agent, or Firm* — Welsh Flaxman & Gitler LLC

(57) ABSTRACT

The colostomy balloon plug has three parallel conduits with a combined charcoal and hydrophobic filter at one end of the largest central first conduit. The largest central first conduit is open at one end and has the combined charcoal and hydrophobic filter at its other end, for elimination of bowel gas. A shorter parallel second conduit terminates on one end in a first balloon and on a second end in a first one-way valve. A shortest parallel third conduit terminates on one end in a second balloon and on a second end in a second one-way valve. A syringe and extension conduit is selectively attached to the two one-way valves. Air, saline solution or sterilized water can be introduced from the syringe through the one-way valves of the extension conduit to inflate the two balloons about the largest central first conduit. The one-way valves prevent deflation of the balloons unless the shorter or shortest parallel conduits are cut to allow the fluid from the two balloons to exit and deflate the balloons.

7 Claims, 3 Drawing Sheets

(56) References Cited

U.S. PATENT DOCUMENTS

| | | | | |
|---|---|---|---|---|
| 4,808,165 A | * | 2/1989 | Carr | A61M 25/1018 604/100.02 |
| 5,261,898 A | * | 11/1993 | Polin | A61F 2/0013 604/327 |
| 6,033,390 A | * | 3/2000 | von Dyck | A61F 5/441 600/29 |
| 6,350,255 B1 | * | 2/2002 | von Dyck | A61F 5/441 604/332 |
| 6,485,476 B1 | * | 11/2002 | von Dyck | A61F 5/441 600/29 |
| 6,595,971 B1 | * | 7/2003 | von Dyck | A61F 5/442 604/334 |
| 2002/0077611 A1 | * | 6/2002 | von Dyck | A61F 5/442 604/333 |
| 2003/0181879 A1 | * | 9/2003 | Mulhauser | A61F 5/445 604/332 |
| 2005/0054996 A1 | * | 3/2005 | Gregory | A61F 5/445 604/317 |
| 2005/0113859 A1 | * | 5/2005 | Elliott | A61F 2/0013 606/197 |
| 2007/0051372 A1 | * | 3/2007 | Tanaka | A61M 16/00 128/207.14 |
| 2007/0207186 A1 | * | 9/2007 | Scanlon | A61F 2/07 424/424 |
| 2008/0312614 A1 | | 12/2008 | Ferko | |
| 2009/0216206 A1 | * | 8/2009 | Nishtala | A61M 39/10 604/327 |
| 2010/0280489 A1 | * | 11/2010 | Nishtala | A61M 3/0283 604/514 |
| 2011/0282311 A1 | * | 11/2011 | Nishtala | A61M 1/0019 604/332 |
| 2011/0306823 A1 | | 12/2011 | Gobel et al. | |
| 2013/0060212 A1 | | 3/2013 | Hanuka et al. | |
| 2013/0197458 A1 | * | 8/2013 | Salama | A61F 5/4405 604/335 |
| 2013/0304008 A1 | * | 11/2013 | Hanuka | A61F 5/4401 604/334 |
| 2015/0174385 A1 | * | 6/2015 | Park | A61B 17/1114 604/540 |
| 2016/0287428 A1 | * | 10/2016 | Eggert | A61F 5/4405 |
| 2017/0135846 A1 | * | 5/2017 | Weiss | A61F 5/445 |
| 2017/0189663 A1 | * | 7/2017 | Kantrowitz | A61M 39/0247 |
| 2017/0367871 A1 | * | 12/2017 | Dinakara | A61F 5/445 |

FOREIGN PATENT DOCUMENTS

| | | |
|---|---|---|
| EP | 2 856 985 A1 | 4/2015 |
| WO | 2011/139498 A1 | 11/2011 |

* cited by examiner

COLOSTOMY BALLOON PLUG

FIELD OF THE INVENTION

Anal or colostomy plugs are medical devices that allow air in the anal cavity and block leaks from the anal cavity offering a patient a few hours of a fecal incontinence free life. Patients with mild bowel incontinence, who may just have streaks of stool passing involuntarily, usually find these protective products very convenient and efficient.

BACKGROUND OF THE INVENTION

Millions of people suffer with the condition of bowel incontinence. The lack of bowel control causes people embarrassment and unsanitary episodes, quite often leading to social isolation. Treatments for the condition range from conservative treatment to radical treatment such as surgery. However, many patients do not respond to conservative treatment and, for various reasons, are not candidates for surgery.

The prior art discloses devices which are used to help sufferers of bowel incontinence with devices to control the condition in order to lead a normal lifestyle. One such device is disclosed in U.S. Pat. No. 4,831,422 (Fisher et al). The device is a probe having dual multiple parallel conduits and one inflatable balloon. The transmission and monitoring of reflected (Infrared) IR light generates an alarm signal when a predetermined amount of reflected IR light is measured. IR light is reflected in response to fecal mass.

Another device is a colostomy balloon catheter that has multiple parallel conduits with a hydrophobic filter as disclosed in U.S. Pat. No. 8,282,597 (Elliott et al.) The multiple parallel conduits are divided into two parallel conduits. A first conduit terminates in a one-way valve. A syringe is attached to the one-way valve. Air, saline solution or sterilized water can be introduced through the one-way valve and inflate the balloon about the two parallel conduits. The second parallel conduit terminates in a charcoal filter for elimination of bowel gas. The one-way valve prevents deflation of the balloon unless the conduit is cut to allow the fluid from the balloon to exit and deflate the balloon.

Most bowel control devices include electronics for sensing and alerting the user to the presence of fecal mass to avoid incontinent episodes. There is a need in the prior art for an inexpensive, colostomy balloon plug which can be used to prevent incontinent episodes. The plug can be used in both the rectum and in a stoma.

SUMMARY OF THE INVENTION

The colostomy balloon plug device including a proximal end and a distal end, comprises three parallel conduits including a largest central first conduit, a shorter parallel second conduit and a shortest parallel third conduit, wherein the largest central first conduit having a proximal first end and a distal second end. A first balloon is provided surrounding the largest central first conduit and the shorter parallel second conduit at the distal end of the colostomy balloon plug device. A second balloon is provided surrounding the three parallel conduits at a central portion of the colostomy balloon plug device between the distal end and the proximal end of the colostomy balloon plug device. The second shorter parallel second conduit includes a first end and a second end, the shorter parallel second conduit being in fluid communication with the first balloon on the first end of the shorter parallel second conduit and in communication with a first one-way valve on the second end of the shorter parallel second conduit. The shortest parallel third conduit includes a first end and a second end. The shortest parallel third conduit is in fluid communication with the second balloon on the first end of the shortest parallel third conduit and is in communication with a second one-way valve on the second end of the shortest parallel third conduit.

Two inflatable balloons are provided to allow the colostomy balloon plug device to be held securely in the rectum of a patient. The two balloons are respectively provided at one end of the colostomy balloon plug device and along the body of the colostomy balloon plug device. The colostomy balloon plug device is divided into the three parallel conduits, two of the conduits are used to pass a fluid or gas to inflate the balloons and the other conduit is larger and centrally positioned to allow gas to leave the rectum or stoma. The two balloons are placed on the outside of the device around the one of the smaller conduits and the central larger conduit at one end of the device and around all three of the conduits at a point near a central section of the colostomy balloon plug device. The two smaller conduits each have a balloon on one end and terminate in a one-way valve, or a male female connection on their other end. A syringe can be attached to the end of the smaller conduits that terminate in the one-way valve or the luer-lock type connector. Air, saline solution or sterilized water can be introduced using the syringe to thereby inflate the two balloons about the multiple parallel conduits. A first balloon, which is closest to the distal end of the colostomy balloon plug device, inflates to a diameter between 3.5 cm and 4.5 cm. The second balloon, which is located at approximately the center of the colostomy balloon plug device, inflates to a diameter of from 1.5 cm to 3.0 cm about all three of the parallel conduits. The largest central conduit is open at the end that is inserted into the rectum or stoma of a patient and terminates in a combined hydrophobic and charcoal filter for elimination of bowel gas and the like, at the other end. The one-way valves located along the ends of the two smaller conduits prevent deflation of the balloons. Cutting of the smaller two parallel conduits allow the fluid or air from the inflated balloons to exit and deflate the balloons.

It is an object of the invention to provide an inexpensive colostomy balloon plug device.

It is a further object of the invention to provide a colostomy balloon plug device having two one-way valves that control inflation of the two balloons about the body of the plug device.

It is yet another object of the invention to provide a plug device which must be destroyed by cutting of the two smaller conduits to allow removal to ensure only a single use.

These and other objects of the invention will become apparent to one of ordinary skill in the art after reading the disclosure of the invention.

DETAILED DESCRIPTION OF THE INVENTION

Figure 1:
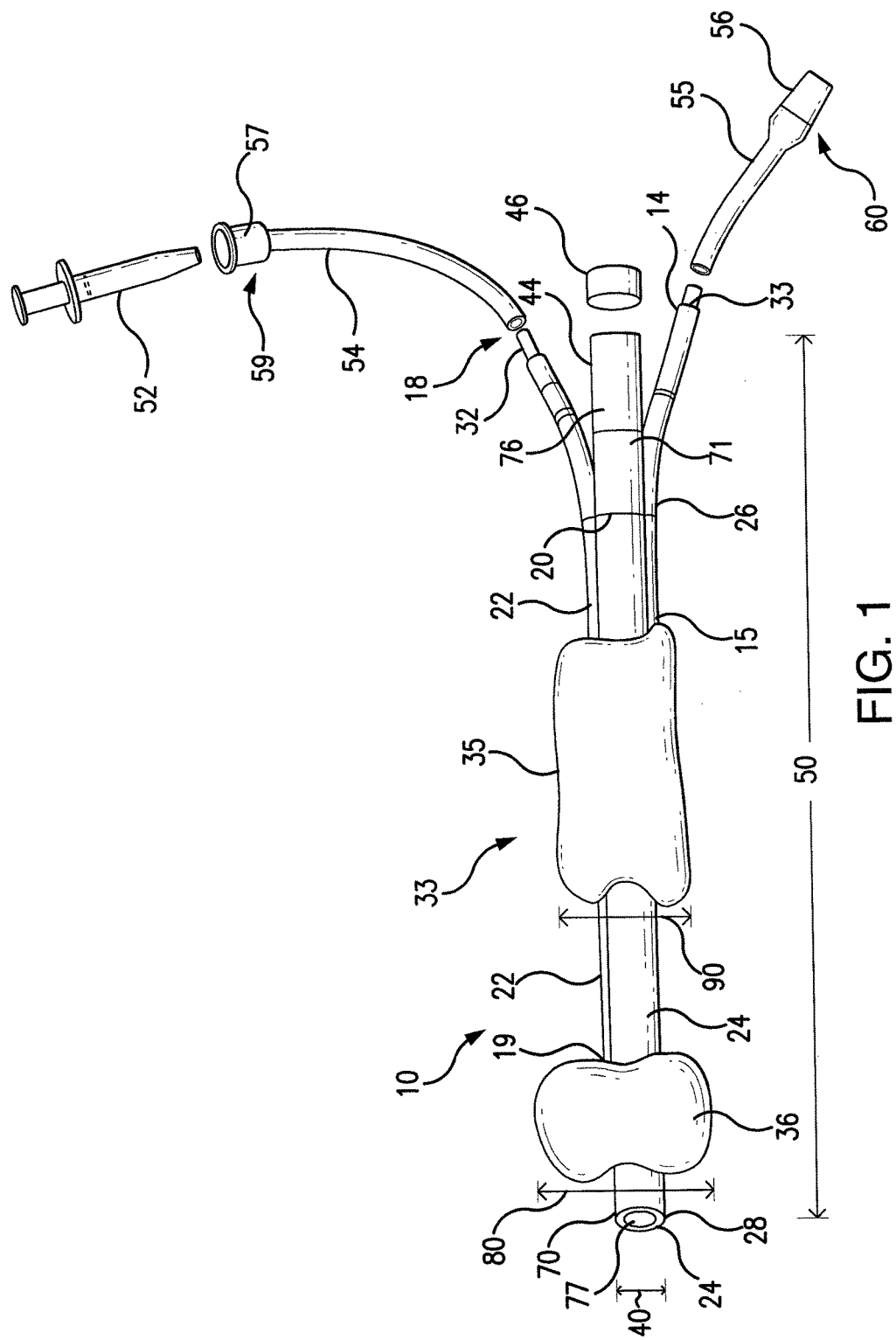
FIG. 1 is a side view of the colostomy balloon plug of the invention.

A colostomy balloon plug device 10 includes a distal end 70 and a proximal end 71. The colostomy balloon plug device 10 is provided having three parallel conduits 22, 24, 26. The colostomy balloon plug device 10 includes a first balloon 36 surrounding the colostomy balloon plug device 10 near the distal end 70 thereof and surrounds two of the parallel conduits 22, 24. The first balloon 36 has a diameter 80 ranging from 3.5 cm to 4.5 cm upon inflation. A second balloon 35 is provided surrounding a central portion 42 of the colostomy balloon plug device 10, and as such surrounds a central portion of a largest central first conduit 24 and a shorter parallel second conduit 22 and is located at a first end 15 of a shortest parallel third conduit 26. As such, the second balloon 35 is positioned between the distal end 70 and the proximal end 71 of the colostomy balloon plug device 10. The second balloon 35 has a diameter 90 ranging from 1.5 cm to 3.0 cm upon inflation.

The three parallel conduits 22, 24, 26 are comprised of the largest central first conduit 24, the shorter parallel second conduit 22 and the shortest parallel third conduit 26. The largest central first conduit 24 includes a distal first end 28 and a proximal second end 76. The largest central first conduit 24 has an overall length 50 ranging from 4.0 cm to 10 cm.

The shorter parallel second conduit 22 includes a first end 19 and a second end 18. The shorter parallel second conduit 22 is in fluid communication with the first balloon 36 on the first end 19 of the shorter parallel second conduit 22 and in communication with a first one-way valve 31 on the second end 18 of shorter parallel second conduit 22.

The shortest parallel third conduit 26 includes a first end 15 and a second end 14. The shortest parallel third conduit 26 is in fluid communication with the second balloon 35 on the first end 15 of the shortest parallel third conduit 26 and in communication with a second one-way valve 35 on the second end 14 of the shortest parallel third conduit 26.

Referring to FIG. 1, and as discussed above, the colostomy balloon plug device 10 is formed by the three parallel conduits 22, 24, 26 forming the body 20 of the device. The overall length 50 of the body 20 of the colostomy balloon plug device 10 ranges from 4 cm to 10 cm depending on size of a patient. The largest central first conduit 24 has a diameter 40 of approximately 1 cm. The shorter parallel second conduit 22 and the shortest parallel third conduit 26 each have a diameter of approximately 1 mm.

The largest central first conduit 24 terminates with an opening 29 at distal first end 28 of the largest central first conduit 24. Spaced from the distal first end 28 and encircling the body 20 of the colostomy balloon plug device 10 at the distal end 70 thereof, in particular, encircling the largest central first conduit 24 and the second shorter conduit 22, is a first balloon 36 with a diameter 80, when inflated, ranging from 3.5 cm-4.5 cm. The first balloon 36 is in fluent communication with the second shorter parallel conduit 22 at the first end 19 of the shorter parallel second conduit 22. The shorter parallel second conduit 22 extends from the first balloon 36 to, and terminates in, a first one-way valve 32 on the second end 18 of the shorter parallel second conduit 22. The first one-way valve 32 is oriented to prevent the discharge of liquid or air from the first balloon 36 once the first balloon 36 has been inflated as described below.

Along the body 20 of the three parallel conduits 22, 24, 26 is a second balloon 35 which is in fluid communication with the shortest parallel third conduit 26. The second balloon 35 is proximally positioned relative to the first balloon 36 and is therefore positioned along the colostomy balloon plug device 10 along a central portion 42 thereof. The second balloon 35 encircles the body 20 of the colostomy balloon plug device 10 at the central portion 42 and consequently encircles each of the three parallel conduits 22, 24, 26. The second balloon 35, when inflated, has a diameter 90 ranging from 1.5 cm-3.0 cm. The shortest parallel third conduit 26 is in fluent communication with the second balloon 35 at the first end 15 of the shortest parallel third conduit 26. The shortest parallel third conduit 26 extends from the second balloon 35 to, and terminates in, a second one-way valve 33 at the second end 14 of the shortest parallel third conduit 26. The second one-way valve 33 is oriented to prevent the discharge of liquid or air from the second balloon 35 once the second balloon has been inflated as described below.

Figure 2:
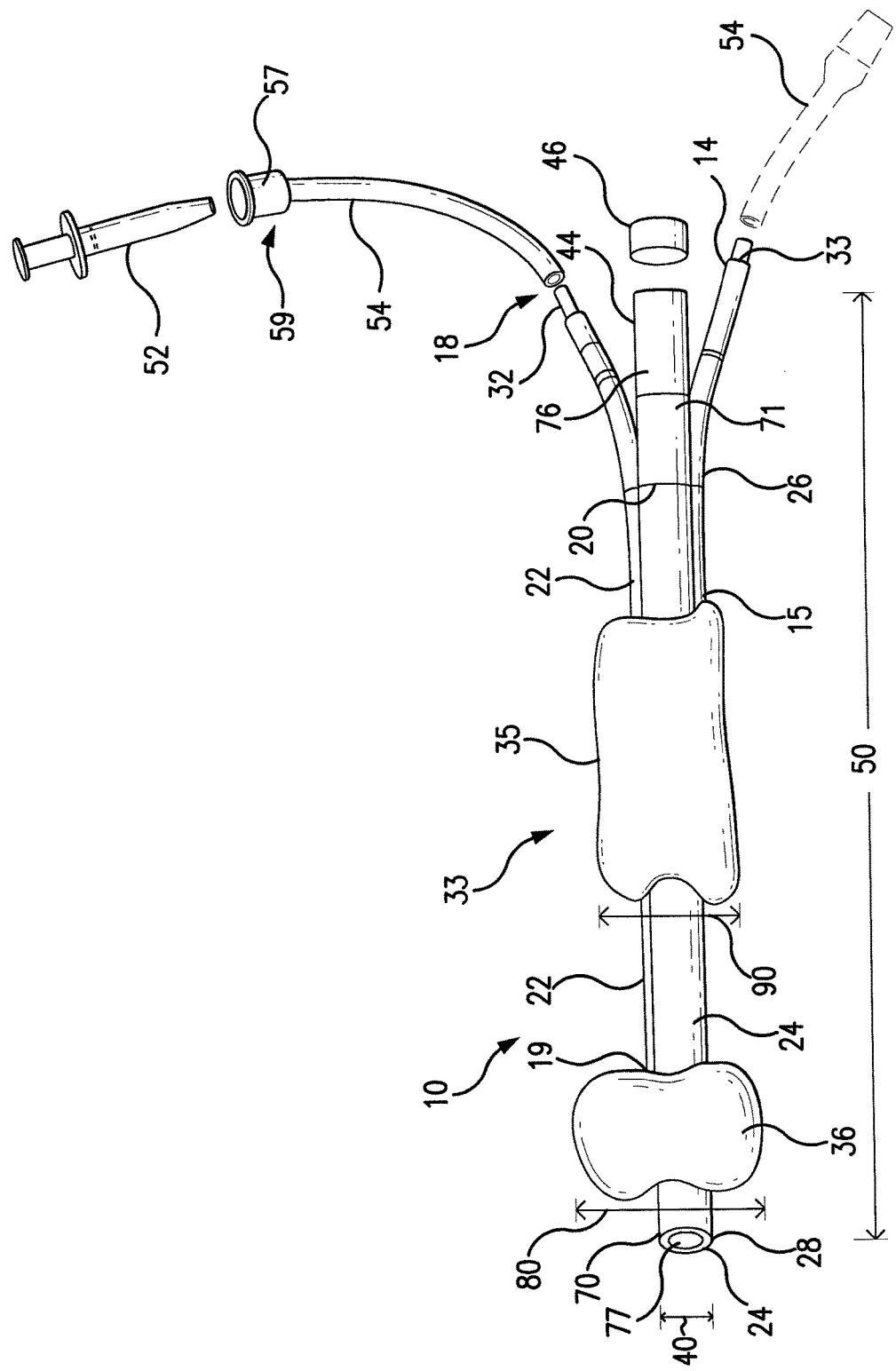
FIG. 2 is an alternate embodiment of the colostomy balloon plug of the invention.

A syringe 52 is provided for connection to a first extension conduit 54. The end of the first extension conduit 54 opposite the syringe is then connected to the one-way valve 32, which is preferable a luer-lock type connection, located on the second end 18 of the shorter parallel second conduit 22. The syringe 52 is also provided for connection to a second extension conduit 55, the opposite end of which is connected to the second one-way valve 33 located on the second end 14 of the shortest parallel third conduit 26. The first and second extension conduits 54 and 55 have a diameter of approximately 2 mm. In the alternative, and with reference to FIG. 2, one extension conduit can be used for sequential connection to each of the shorter parallel second conduit 22 and the shortest parallel third conduit 26, via male/female connector, for inflation of the first and second balloons 36, 35.

Figure 3:
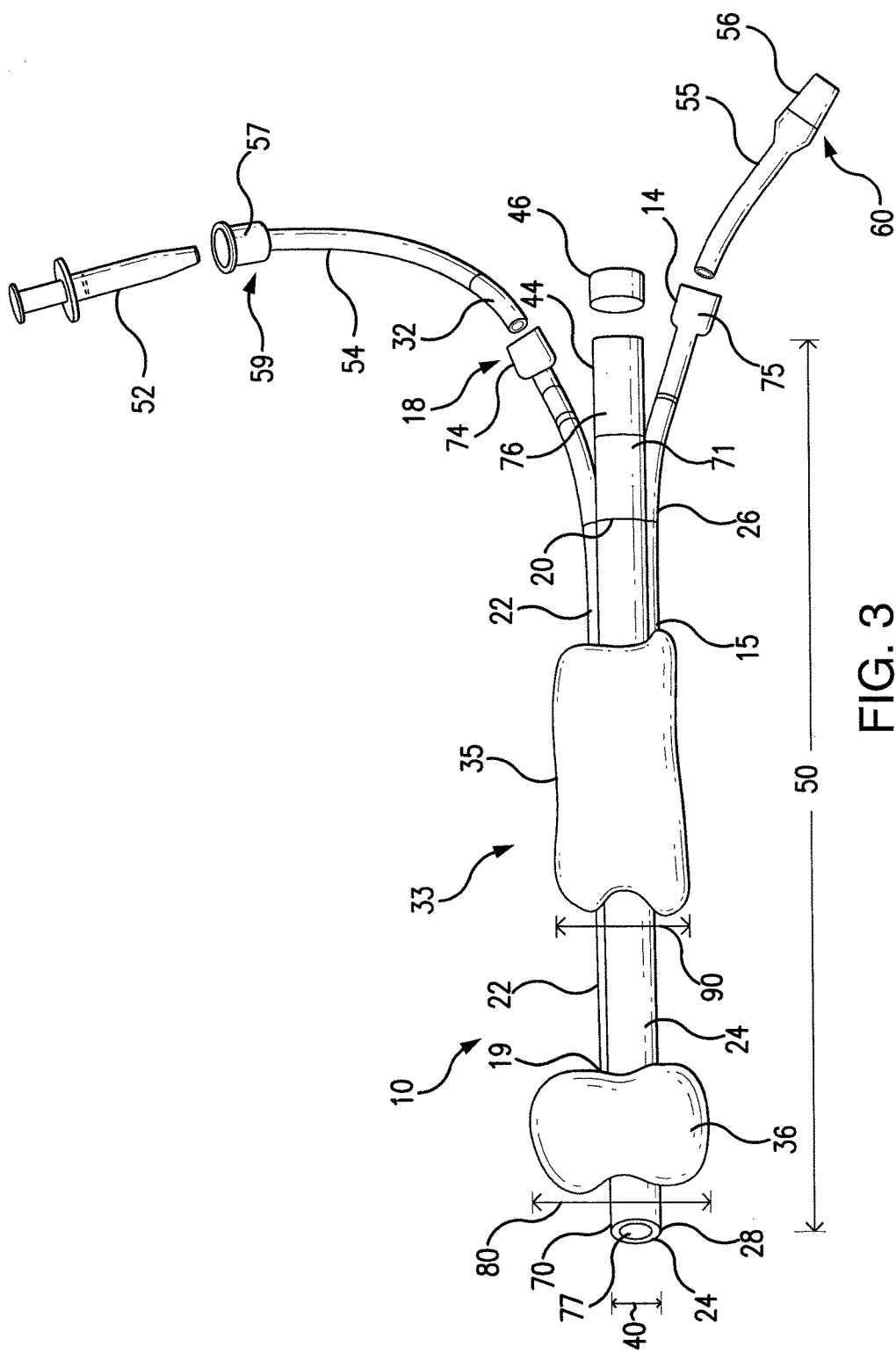
FIG. 3 is an alternate embodiment of the colostomy balloon plug of the invention.

The syringe 52 may be a bulb or plunger type. In practice, the syringe 52 is charged with 40 cubic centimeters (cc) to 50 cc of air, saline or sterilized water. After the first and the second conduits 54, 55 have been connected to the first and second one-way valves 32, 33 of the shorter parallel second conduit 22 and the shortest parallel third conduit 26, the syringe 52 is used to inflate the first and second balloons 36, 35 as will be explained below in greater detail. In the alternative, and as shown with reference to FIG. 3, the first and second one-way valves 32, 33, can be replaced with male/female luer-type connectors 74, 75 at the respective ends 18, 14 of the shorter parallel second conduit 22 and the shortest parallel third conduit 26. When this alternative embodiment is employed the first and second one-way valves 32, 33 are located at the end of the extension conduits 54, 55.

Luer-lock connections 56, 57 are provided at the ends 59, 60 of the extension conduits 54, 55 to enable connection of the syringe 52 to the extension conduits 54, 55. A luer-lock connection is one that contains grooves so that a syringe 52 can be securely screwed to it. The luer-lock type connections 56, 57 are located at the ends 59, 60 of the extension conduits 54, 55.

As mention above, the largest central first conduit 24 includes a distal first end 28 and a proximal second end 76. The distal first end 28 of the largest central first conduit 24 defines a hydrophobic tip 77 at the distal end 70 of the colostomy balloon plug device 10. Secured to the proximal second end 76 of the largest central first conduit 24 is a filter 44, which is therefore located at the proximal end 71 of the colostomy balloon plug device 10. The filter 44 is preferably formed by a charcoal filter sandwiched by two hydrophobic filters and such defines a combined charcoal and hydrophobic filter. A filter cap 46 can be used to close off the filter 44 at the proximal second end 76 of the largest central first conduit 24.

To use the colostomy balloon plug device 10, the user grasps the body 20 of the three parallel conduits 22, 24, 26 below the first balloon 36, that is, between the first balloon 36 and the proximal end 71 of the colostomy balloon plug device 10. The distal first end 28 of the largest central first conduit 24, and consequently the distal end 70 of the colostomy balloon plug device 10 is inserted into the rectum or stoma, of a patient, approximately three inches or to a depth recommended by the doctor such that the first balloon 36 is aligned with the sphincter. Once in place, and with the first extension conduit 54 secured to the shorter parallel second conduit 22, the syringe 52 is inserted into the luer-lock type connection 57 of the first extension conduit 54 to inject the air, sterile water, or saline solution through the shorter parallel second conduit 22 to inflate the balloon 36 with 40 cc to 50 cc of air, sterile water, or saline solution so as to expand the first balloon 36 to a diameter 80 ranging from 3.5 cm to 4.5 cm. The first extension conduit 54 can be attached before or after the device 10 is inserted. Once inflated, the first balloon 36 is seated against the sphincter. After inflation, and with the second extension conduit 55 secured to the shortest parallel third conduit 26, the syringe 52 is inserted into the Luer-lock type connection 56 of the second extension conduit 55 to inject the air, sterile water or saline solution through the third shortest parallel conduit 26 to inflate the second balloon 35 with 40 cc to 50 cc of air, sterile water, or saline solution so as to expand the second balloon 35 to a diameter 90 ranging from 1.5 cm to 3.0 cm and to prevent the device 10 from falling out of the rectum or stoma of the patient. The syringe 52 is then disconnected from the luer-lock type connection 56.

The colostomy balloon plug device 10 is particularly useful for those patients who are able to maintain a regular schedule of bowel movements. At the appropriate time, as scheduled or as sensed by the user, the colostomy balloon plug device 10 can be moved to allow bowel movement. As mentioned above, the first and second one-way valves 32, 33 do not allow the discharge of liquid or air from the first and second balloons 36, 35. As such, and in order to deflate the balloons 36, 35 for the removal of the colostomy balloon plug device 10, the user must cut the second shorter and third shortest parallel conduits 22, 26 at a location distal to the respective first and second one-way valves 32, 33 so that fluid within the first and second balloons 36, 35 is allowed to exit through the shorter parallel second conduit 22 and the shortest third parallel conduit 26. Once deflated, the colostomy balloon plug device 10 can be removed.

The largest central first conduit 24 is open at its two ends 28, 76, and gas is, therefore, allowed to pass through the colostomy balloon plug device 10. The tip 77 of the colostomy balloon plug device 10 at the distal first end 28 of the largest central first conduit 24 is preferably formed of silicone. The tip 77 is defined by the opening 29 at the distal first end 28 of the largest central first conduit 24 and allows gases to pass therethrough. The largest central first conduit 24 is also provided with a combined charcoal and hydrophobic filter 44 at its proximal second end 77 to eliminate odors of gases passing through the colostomy balloon plug device 10. An optional cap 46 for the filter 44 can be provided to protect the filter 44.

While the invention has been described with reference to a preferred embodiment, variations and modifications would be apparent to one of ordinary skill in the art. The invention is intended to encompass such variations and modifications without departing from the scope of the invention.

The invention claimed is:

1. A colostomy balloon plug device including a proximal end and a distal end, comprising:
    three parallel conduits including a central first conduit having a distal first end and a proximal second end, a parallel second conduit, and a parallel third conduit, wherein an overall length of the central first conduit is longer than an overall length of the parallel second conduit, and the parallel third conduit has an overall length shorter than the parallel second conduit;
    a first balloon surrounding the central first conduit and the parallel second conduit at the distal end of the colostomy balloon plug device;
    a second balloon surrounding the three parallel conduits at a central portion of the colostomy balloon plug device between the distal end and the proximal end of the colostomy balloon plug device, wherein a diameter of the first balloon, located at the distal end of the colostomy balloon plug device, when inflated is greater than a diameter of the second balloon, located between the distal end and the proximal end of the device, when inflated;
    the parallel second conduit including a first end and a second end, the parallel second conduit being in fluid communication with the first balloon on the first end of the parallel second conduit and in communication with a first one-way valve on the second end of the parallel second conduit;
    the parallel third conduit including a first end and a second end, the parallel third conduit being in fluid communication with the second balloon on the first end of the parallel third conduit and in communication with a second one-way valve on the second end of the parallel third conduit, wherein a first extension conduit with a first luer lock connection is attached to the first one-way valve on the second end of the parallel second conduit and a second extension conduit with a second luer lock connection is attached to the second one-way valve on the second end of the parallel third conduit.

2. The colostomy balloon plug device of claim 1, further comprising a combined charcoal and hydrophobic filter on the proximal second end of the central first conduit and a cap to selectively cover the filter.

3. The colostomy balloon plug device of claim 1, wherein the diameter of the first balloon when inflated ranges from 3.5 cm to 4.5 cm.

4. The colostomy balloon plug device of claim 1, wherein the diameter of the second balloon when inflated ranges from 1.5 cm to 3.0 cm.

5. The colostomy balloon plug device of claim 1, wherein the parallel second conduit has a diameter of approximately 1.0 mm.

6. The colostomy balloon plug device of claim 1, wherein the parallel third conduit has a diameter of approximately 1.0 mm.

7. The colostomy balloon plug device of claim 1, wherein the central first conduit has the overall length ranging from 4.0 cm to 10.0 cm.

* * * * *